United States Patent
Voice et al.

(10) Patent No.: US 12,237,055 B2
(45) Date of Patent: Feb. 25, 2025

(54) METHOD TO GENERATE HIGHLY ACCURATE THERMODYNAMIC AND PHYSICAL FLUID PROPERTIES OF REAL LIGHT-DISTILLATE FUELS FOR ONE-DIMENSIONAL HYDRAULIC MODELS USING A DETAILED MULTI-COMPONENT SURROGATE FORMULATION APPROACH

(71) Applicant: ARAMCO SERVICES COMPANY, Houston, TX (US)

(72) Inventors: Alexander K. Voice, Detroit, MI (US); Tommy Tzanetakis, Novi, MI (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 1051 days.

(21) Appl. No.: 17/036,359

(22) Filed: Sep. 29, 2020

(65) Prior Publication Data

US 2022/0101957 A1  Mar. 31, 2022

(51) Int. Cl.
G16C 60/00 (2019.01)
G01N 33/28 (2006.01)
G16C 20/30 (2019.01)
G16C 20/40 (2019.01)

(52) U.S. Cl.
CPC ......... G16C 60/00 (2019.02); G01N 33/2852 (2013.01); G16C 20/30 (2019.02); G16C 20/40 (2019.02)

(58) Field of Classification Search
CPC ........ G16C 60/00; G16C 20/30; G16C 20/40; G01N 33/2852
See application file for complete search history.

(56) References Cited

U.S. PATENT DOCUMENTS

2003/0200957 A1* 10/2003 Shinogle .............. F02D 41/365
123/480
2015/0198081 A1* 7/2015 Surnilla .............. F02M 63/029
123/294

OTHER PUBLICATIONS

Ra et al. "A combustion model for multi-component fuels using a physical surrogate group chemistry representation (PSGCR)", Combustion and Flame, (2015), 26 p.*

(Continued)

*Primary Examiner* — Alexander Satanovsky
(74) *Attorney, Agent, or Firm* — Osha Bergman Watanabe & Burton LLP

(57) ABSTRACT

A method for generating a multi-component surrogate is provided. The method includes determining, based on a detailed hydrocarbon analysis, components of a physical fuel sample, selecting, for a hydrocarbon, chemicals from a list of known chemicals in a chemical property database, chemical property correlation software, or chemical process software package, the hydrocarbon having an equivalent molecular structure as each of the chemicals, dividing a concentration of the hydrocarbon in the physical fuel sample into surrogate concentrations corresponding to the chemicals, and generating the multi-component surrogate based at least on the surrogate concentrations, where each of the chemicals represents the hydrocarbon as a surrogate in the multi-component surrogate, and the multi-component surrogate is used to represent the physical fuel sample in a one-dimensional (1D) hydraulic modeling software to model a direct injection (DI) system.

20 Claims, 10 Drawing Sheets

(56) References Cited

OTHER PUBLICATIONS

Poon et al., "Development of multi-component diesel surrogate fuel models—Part II: Validation of the integrated mechanisms in 0-D kinetic and 2-D CFD spray combustion simulations", Fuel 181 (2016), pp. 120-130.*

Prak et al., "Formulation of Surrogate Fuel Mixtures Based on Physical and Chemical Analysis of Hydrodepolymerized Cellulosic Diesel Fuel", ACS Publications, Energy Fuels 2016, 30, 9, pp. 7331-7341.*

Sun et al., "Development of surrogate fuels for heavy fuel oil in marine engine", Energy, vol. 185, 2019, pp. 961-970.*

Gokul Vishwanathan et al., "Development of a Practical Soot Modeling Approach and Its Application To Low-Temperature Diesel Combustion", Combust. Sci. and Tech., 182: 1050-1082, 2010.*

Sarathy, S. Mani et al., "Recent progress in gasoline surrogate fuels," Progress in Energy and Combustion Science, ScienceDirect, Elsevier Ltd., vol. 65, 2018, Available Online Dec. 2017, pp. 67-108 (42 pages).

Jameel, Abdul Gani Abdul et al., "A minimalist function group (MFG) approach for surrogate fuel formulation," Combustion and Flame, ScienceDirect, Elsevier Inc., Mar. 2018, vol. 192, pp. 250-271 (22 pages).

Ahmed, Ahfaz et al., "A computational methodology for formulating gasoline surrogate fuels with accurate physical and chemical kinetic properties," Fuel, ScienceDirect, Elsevier Ltd., vol. 43, 2015, Available Online Nov. 2014, pp. 290-300 (11 pages).

Payri, Raul et al. "Rate of injection modelling for gasoline direct injectors," Energy Conversion and Management, ScienceDirect, Elsevier Ltd., vol. 166, May 2018, pp. 424-432 (9 pages).

Elwardany, Ahmed et al., "Modeling of Heating and Evaporation of Face I Gasoline Fuel and its Surrogates," SAE Technical Paper 2016-01-0878, SAE International, Apr. 2016 (7 pages).

Wang, Hai et al., "A physics-based approach to modeling real-fuel combustion chemistry—I. Evidence from experiments, and thermodynamic, chemical kinetic and statistical considerations," Combustion and Flame, ScienceDirect, Elsevier Inc., 2018, pp. 1-18, URL: <https://doi.org/10.1016/j.combustflame.2018.03.019> (18 pages).

Su, Xingyuan et al., "A Surrogate Fuel Formulation Approach for Real Transportation Fuels with Application to Multi-Dimensional Engine Simulations," SAE Technical Paper 2014-01-1464, SAE International, Apr. 2014, pp. 236-249 (14 pages).

Ra, Youngchul and Rolf D. Reitz, "A combustion model for multi-component fuels using a physical surrogate group chemistry representation (PSGCR)," Combustion and Flame, ScienceDirent, Elsevier Inc., 2015, pp. 1-26, URL: <http://dx.doi.org/10.1016/j.combustflame.2015.05.014> (26 pages).

Wu, Zhiyong et al., "Surrogate Formulation for Marine Diesel Considering Some Important Fuel Physical?Chemical Properties," Engery & Fuels, ACS Publications, American Chemical Society, vol. 33, Mar. 2019, pp. 3539-3550 (12 pages).

* cited by examiner

311

① Detailed Hydrocarbon Analysis Results

| GROUP | COMPONENT | %VOL. |
|---|---|---|
| Paraffin | Propane | 0.018 |
| | n-Butane | 3.157 |
| | n-Pentane | 8.054 |
| | n-Hexane | 8.426 |
| | n-Heptane | 8.002 |
| | n-Octane | 6.098 |
| | n-Nonane | 0.409 |
| | n-Decane | 0.009 |
| | n-Undecane | 0.009 |
| | n-Dodecane | 0.002 |
| i-Paraffins | i-Butane | 0.399 |
| | i-Pentane | 6.161 |
| | 2,2-Dimethylbutane | 0.314 |
| | 2,3-Dimethylbutane | 0.693 |
| | 2-Methylpentane | 5.139 |
| | 3-Methylpentane | 3.158 |
| | 2,4-Dimethylpentane | 0.527 |
| | 2,2,3-Trimethylbutane | 0.036 |

② Generate Surrogate

...

Complete list not shown, includes over a hundred individual components and several other chemical groups

*FIG. 3B*

Detailed Multi-Component Surrogate Listing — 312

| COMPONENT | %VOL | COMPONENT | %VOL |
|---|---|---|---|
| n-Butane | 4.116 | m-Xylene | 2.702 |
| n-Pentane | 7.794 | p-Xylene | 1.198 |
| i-Pentane | 5.781 | o-Xylene | 0.686 |
| Cyclopentane | 0.289 | n-Octane | 6.198 |
| n-Hexane | 8.663 | 3-Mheptane | 6.089 |
| 2-Mpentane | 5.186 | 1-tr3-MCC6 | 1.613 |
| 3-Mpentane | 3.18 | 4-Mheptane | 1.042 |
| 2-Mheptane | 3.119 | 3-Ehexane | 0.937 |
| Cyclohexane | 2.121 | Ecycheptane | 0.913 |
| Mcyclopentan | 1.914 | 24-Mhexane | 0.608 |
| 23-Mbutane | 0.715 | 25-Mhexane | 0.522 |
| Benzene | 0.687 | cis-3-Octene | 0.435 |
| 22-Mbutane | 0.277 | n-Pcycpentan | 0.374 |
| n-Heptane | 8.093 | 23-Mhexane | 0.333 |
| Mcyclohexane | 5.092 | E-Benzene | 0.326 |
| 2-Mhexane | 4.688 | 113-MCC5 | 0.213 |
| Toluene | 3.497 | 1tr2ci4-MCC5 | 0.211 |
| 3-Mhexane | 3.348 | tr2-Octene | 0.414 |
| 1-tr2-MCC5 | 0.722 | 3-Moctane | 0.682 |
| 24-Mpentane | 0.543 | 4-Moctane | 0.637 |
| 1-tr3-MCC5 | 0.369 | 25-Mheptane | 2.284 |
| 1-ci3-MCC5 | 0.354 | | |
| 1-Heptene | 0.032 | | |

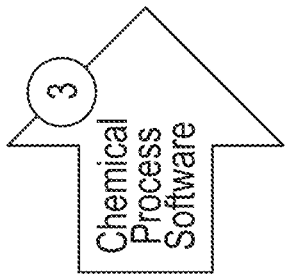

*FIG. 3B (Continued)*

Fluid Properties from Chemical Process Software

| State | 1 - Temperature | 1 - Pressure | 1 - Phase Viscosity (Liquid Phase) |
|---|---|---|---|
| | C | bar_g | cP |
| Case 1 | 20 | 0 | 0.4141 |
| Case 2 | 20 | 20 | 0.4149 |
| Case 3 | 20 | 40 | 0.4158 |
| Case 4 | 20 | 60 | 0.4166 |
| Case 5 | 20 | 80 | 0.4175 |
| Case 6 | 20 | 100 | 0.4183 |
| Case 7 | 20 | 120 | 0.419 |
| Case 8 | 20 | 140 | 0.4198 |
| Case 9 | 20 | 160 | 0.4205 |
| Case 10 | 20 | 180 | 0.4213 |
| Case 11 | 20 | 200 | 0.422 |
| Case 12 | 20 | 220 | 0.4227 |

313

Generate Property Tables ④

METHOD TO GENERATE HIGHLY ACCURATE THERMODYNAMIC AND PHYSICAL FLUID PROPERTIES OF REAL LIGHT-DISTILLATE FUELS FOR ONE-DIMENSIONAL HYDRAULIC MODELS USING A DETAILED MULTI-COMPONENT SURROGATE FORMULATION APPROACH

BACKGROUND

Direct injection (DI) is a method and system of forming fuel mixtures for internal combustion engines operating based on gasoline compression ignition (GCI). In particular, the fuel is injected into the combustion chamber for compression ignition instead of injecting into the air intake manifold using port fuel injection systems. Various components of the DI fuel system (e.g., pump, injector, accumulator, tubing, etc.) may be modeled based on fuel surrogates to refine the structural features for improving engine performance. Fuel surrogates are mixtures of fuel compounds that are designated to emulate physical properties (e.g., vapor pressure, etc.) and/or chemical properties (e.g., combustion characteristics such as laminar flame speed, etc.) of a more complex fuel.

SUMMARY

In general, in one aspect, the invention relates to a method for generating a multi-component surrogate. The method includes determining, based on a detailed hydrocarbon analysis, a plurality of components of a physical fuel sample, selecting, by a computer processor and for a first hydrocarbon of the plurality of hydrocarbons, a first plurality of chemicals from a list of known chemicals in a chemical property database, chemical property correlation software, or chemical process software package, the first hydrocarbon having a first equivalent molecular structure as each of the first plurality of chemicals, dividing, by the computer processor, a first concentration of the first hydrocarbon in the physical fuel sample into a first plurality of surrogate concentrations corresponding to the first plurality of chemicals, and generating, by the computer processor, the multi-component surrogate based at least on the first plurality of surrogate concentrations, wherein each of the first plurality of chemicals represents the first hydrocarbon as a surrogate in the multi-component surrogate, and wherein the multi-component surrogate is used to represent the physical fuel sample in a one-dimensional (1D) hydraulic modeling software to model a direct injection (DI) system.

In general, in one aspect, the invention relates to a computer system for generating a multi-component surrogate. The computer system includes a processor and a memory coupled to the processor and storing instructions. The instructions, when executed by the processor, include functionality for determining, based on a detailed hydrocarbon analysis, a plurality of hydrocarbons of a physical fuel sample, selecting, for a first hydrocarbon of the plurality of hydrocarbons, a first plurality of chemicals from a list of known chemicals of a chemical process software package, the first hydrocarbon having a first equivalent molecular structure as each of the first plurality of chemicals, dividing a first concentration of the first hydrocarbon in the physical fuel sample into a first plurality of surrogate concentrations corresponding to the first plurality of chemicals, and generating the multi-component surrogate based at least on the first plurality of surrogate concentrations, wherein each of the first plurality of chemicals represents the first hydrocarbon as a surrogate in the multi-component surrogate, and wherein the multi-component surrogate is used to represent the physical fuel sample in a one-dimensional (1D) hydraulic modeling software to model a direct injection (DI) system.

In general, in one aspect, the invention relates to a non-transitory computer readable medium storing instructions executable by a computer processor for generating a multi-component surrogate. The instructions include functionality for determining, based on a detailed hydrocarbon analysis, a plurality of hydrocarbons of a physical fuel sample, selecting, for a first hydrocarbon of the plurality of hydrocarbons, a first plurality of chemicals from a list of known chemicals of a chemical process software package, the first hydrocarbon having a first equivalent molecular structure as each of the first plurality of chemicals, dividing a first concentration of the first hydrocarbon in the physical fuel sample into a first plurality of surrogate concentrations corresponding to the first plurality of chemicals, and generating the multi-component surrogate based at least on the first plurality of surrogate concentrations, wherein each of the first plurality of chemicals represents the first hydrocarbon as a surrogate in the multi-component surrogate, and wherein the multi-component surrogate is used to represent the physical fuel sample in a one-dimensional (1D) hydraulic modeling software to model a direct injection (DI) system.

Other aspects and advantages will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1:
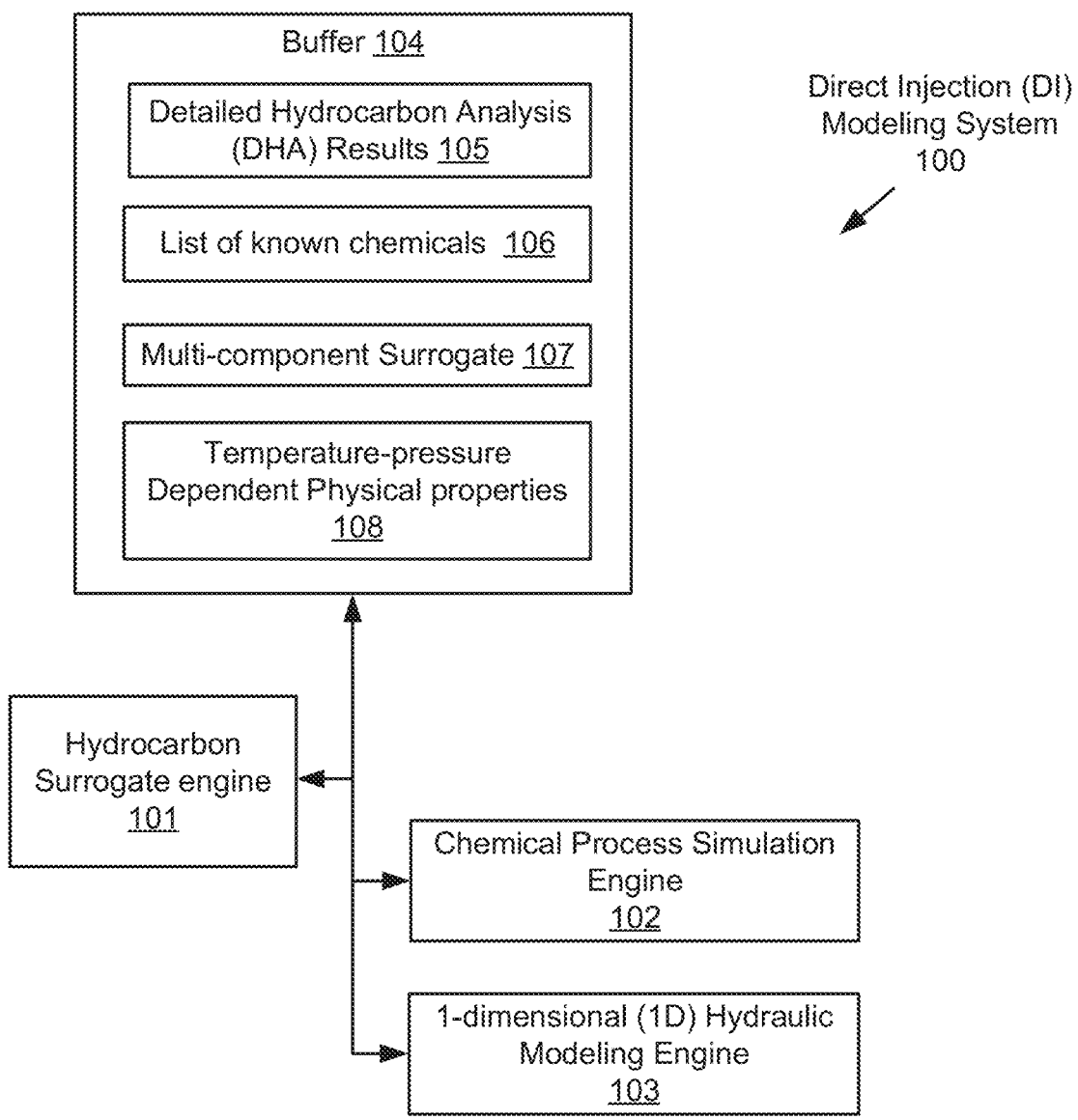
FIG. 1 shows a system in accordance with one or more embodiments.

Specific embodiments of the disclosure will now be described in detail with reference to the accompanying figures. Like elements in the various figures are denoted by like reference numerals for consistency.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Embodiments of the invention provide a method, a system, and a non-transitory computer readable medium for generating accurate physical properties for a light-distillate fuel over a given set of temperature and pressure conditions. More specifically, the physical properties are formatted into the tables and equation constants that are used as input data to an existing 1-dimensional (1D) hydraulic modeling software package. Initially, all of the individual chemical components (e.g., hydrocarbons) and corresponding concentrations are identified in a real fuel sample. The identification may be performed using an existing standardized test method referred to as the detailed hydrocarbon analysis (DHA). The results from the DHA are used to generate a detailed multi-component surrogate that closely resembles the chemical constituents of the real fuel sample. In one or more embodiments of the invention, generating the multi-component surrogate is based at least on the molecular structure, carbon number and type, and other characteristics of hydrocarbons that are not available in the pre-configured chemical template of an existing chemical process simulator software. A set of physical properties of the multi-component surrogate in the liquid and vapor phases is generated over the pressure and temperature ranges of interest. Specifically, the existing chemical process simulation software is used to accurately calculate the thermo-physical properties of the multi-component surrogate. The set of physical properties of the multi-component surrogate is formatted into the tables and equation constants required by the existing 1D hydraulic modeling software package. In one or more embodiments, the output files from the existing chemical process simulation software package are processed to export relevant data to a format recognized by the 1D hydraulic modeling software package.

Turning to FIG. 1, FIG. 1 shows a schematic diagram of a direct injection (DI) modeling system (100) in accordance with one or more embodiments. In one or more embodiments of the invention, the DI modeling system (100) is configured to model the behavior of fuel inside a fuel injector. In particular, the behavior of fuel inside the injector is described based on a single set of accurate thermo-physical properties excluding chemical property consideration (e.g., fuel-air reactivity) in the engine environment. Because the chemical property consideration is excluded, one or more embodiments are able to employ highly detailed fuel surrogates (e.g., including over 100 components) with a very similar, if not identical, component list that advantageously approximates real hydrocarbon fuels. Modeling DI injectors with a 1D hydraulic model using very simple surrogates (e.g., less than 10 components) limits the accurately modeled injection pressure range to below approximately 500 bar. One or more embodiments extends the property specifications of simple fuel surrogates to model prototype injection system hardware over a much higher pressure range (e.g., up to 3000 bar). In particular, the DI modeling system (100) generates a more accurate multi-component surrogate for gasoline that alleviates the calibration efforts needed to refine the 1D hydraulic model. Without the complexity limitation of the simple fuel surrogate, the DI modeling system (100) achieves highly improved accuracy in the calculation of representative fuel properties for subsequent 1D hydraulic modeling steps.

The requirement to model gasoline or light-distillate injection at very high pressures has not been previously considered in the industry. Historically, high pressure fuel system equipment has only been used to enable improved emissions and performance characteristics for engines that use diesel fuel. Current gasoline engines are targeting injection pressures well below those needed in diesel systems. The fuel properties needed to perform 1D diesel and gasoline modeling activities within their respective applications have been well established in the industry without requiring further refinement in existing 1D hydraulic modeling software due to good agreement with experimental results. In particular, the focus of the fuel properties considered in existing 1D hydraulic modeling software is to accurately capture the thermo-physical behavior of fuels in production engines (i.e. the flow and wave dynamics of fuel in conventional gasoline or diesel fuel systems within their respective temperature and pressure ranges).

On the other hand, existing chemical process simulation software was originally developed to calculate the chemical, thermodynamic and physical properties of complex mixtures for use in chemical process modeling and design (i.e., chemical plants, refineries, etc.). As such, existing chemical process simulation software has long been excluded from use in developing alternative fluid models for the injector hardware design and improvement.

In one or more embodiments of the invention, the DI modeling system (100) is used to design and optimize DI engines equipped with high pressure injection components that achieve higher efficiency and lower emissions compared to conventional diesel and gasoline engines, especially with the use of alternative light-distillate fuels other than market gasoline. In particular, the DI modeling system (100) allows a wide variety of light-distillate fuel options to be modeled accurately with the high pressure injection equipment.

As shown in FIG. 1, FIG. 1 illustrates the DI modeling system (100) that has multiple components, including, for example, a buffer (104), a hydrocarbon surrogate engine (101), a chemical process simulation engine (102), and a 1D hydraulic modeling engine (103). Each of these components (101, 102, 103, 104) may be located on the same computing device (e.g., personal computer (PC), laptop, tablet PC, smart phone, multifunction printer, kiosk, server, etc.) or on different computing devices that are connected via a network, such as a wide area network or a portion of Internet of any size having wired and/or wireless segments. Each of these components is discussed below.

In one or more embodiments of the invention, the buffer (104) may be implemented in hardware (i.e., circuitry), software, or any combination thereof. The buffer (104) is configured to store data generated by and/or used by the DI modeling system (100). The data stored in the buffer (104) includes the detailed hydrocarbon analysis (DHA) results (105), the list of known chemicals (106), the multi-component surrogate (107), and the temperature-pressure dependent physical properties (108).

The DHA results (105) are results of performing DHA of a real fuel sample. In one or more embodiments of the invention, the real fuel sample includes light-distillate fuels. The list of known chemicals (106) is a list of industrially important fluids and their mixtures with well-validated properties. The list of known chemicals (106) is included in the toolsets of a commercially available chemical process simulator software package. The multi-component surrogate (107) is a mixture of chemicals selected from the list of known chemicals (106) that collectively emulate thermo-physical properties of the real fuel sample. These chemicals are selected from the list of known chemicals (106) based on having equivalent molecular structures as compared to hydrocarbons in the real fuel sample. The temperature-pressure dependent physical properties (108) are computed characteristics of the real fuel sample that are used as input to a commercially available 1D hydraulic modeling software package.

In one or more embodiments of the invention, each of the hydrocarbon surrogate engine (101), chemical process simulation engine (102), and 1D hydraulic modeling engine (103) may be implemented in hardware (i.e., circuitry), software, or any combination thereof.

In one or more embodiments of the invention, the hydrocarbon surrogate engine (101) is configured to generate the multi-component surrogate (107) by comparing the DHA results and the list of known chemicals (106) based on a pre-determined hierarchy of equivalent molecular structures. The hierarchy is organized based on the molecular structure, carbon number, hydrocarbon type, and other characteristics of hydrocarbons. Molecular structure is a data item that describes the location of constituent atoms in a hydrocarbon or other chemical's molecule. Carbon number is the total number of carbon atoms contained in a hydrocarbon or other chemical's molecule. Hydrocarbon type refers to the type of chemical bonds between the carbon atoms and other parts of the molecule. Hydrocarbon type includes monoaromatic (substituted benzene), naphthalene, fluorene, anthracene, olefin, iso-olefin (alkene or alkyne), olefino-naphthene, mono-naphthene (cycloalkane), decalin, indane, indene, tetralin, paraffin, isoparaffin (alkane), alcohol, ether, ester, ketone, and aldehyde. Alkanes contain only single bonds, alkenes contain a carbon-carbon double bond, alkynes contain a carbon-carbon triple bond, and aromatics contain a benzene ring. Examples of equivalent molecular structure includes stereoisomer, structural isomer, etc. Two molecules are a stereoisomer of each other if they have the same molecular formula and same sequence of bonded atoms, but differ in the three-dimensional (3D) orientations of atoms in space. Two molecules are a structural isomer of each other if they have the same molecular formula, but differ in the type or order of bond connections.

In one or more embodiments of the invention, the chemical process simulation engine (102) is configured to run a chemical process simulator to mathematically model chemical processes, from unit operations to full chemical plants and refineries. Examples of commercially available chemical process simulator software packages include ASPEN HYSYS developed by Aspen Technology, Inc., REFPROP (Reference Fluid Properties) developed by National Institute of Standards and Technology (NIST), etc. The ASPEN HYSYS and REFPROP packages are generally used to calculate the thermodynamic and physical properties of industrially important fluids and their mixtures, such as those contained in the list of known chemicals (106).

In one or more embodiments of the invention, the 1D hydraulic modeling engine (103) is configured to run a 1D hydraulic modeling software package to assess efficacy of DI system component hardware design changes to improve automotive fuel system performance. For example, the 1D hydraulic modeling engine (103) uses the 1D hydraulic modeling software package to calculate the interaction between mechanical components (e.g., pumps, injectors, accumulators, etc.) and a fluid medium (e.g., liquid, vapor, and combinations thereof). A key aspect of the 1D hydraulic modeling is to have accurate thermodynamic and physical properties for the fluid. Existing 1D modeling software packages have, in their toolsets, well-validated properties for commercial fuels (e.g., gasoline, diesel, kerosene, etc.) within the current temperature and pressure ranges of interest. The 1D hydraulic modeling engine (103) uses the temperature-pressure dependent physical properties (108) of a custom fluid (e.g., unconventional light distillate fuel) with extended operating range to augment the existing toolsets.

In one or more embodiments, the DI modeling system (100), more specifically, the hydrocarbon surrogate engine (101), performs the functionalities described above using the method described in reference to FIG. 2 below.

Although the DI modeling system (100) is shown as having three engines (101, 102, 103), in other embodiments of the invention, the DI modeling system (100) may have more or fewer engines and/or more or fewer other components. Further, the functionality of each component described above may be split across components. Further still, each component (101, 102, 103) may be utilized multiple times to carry out an iterative operation.

Figure 2:
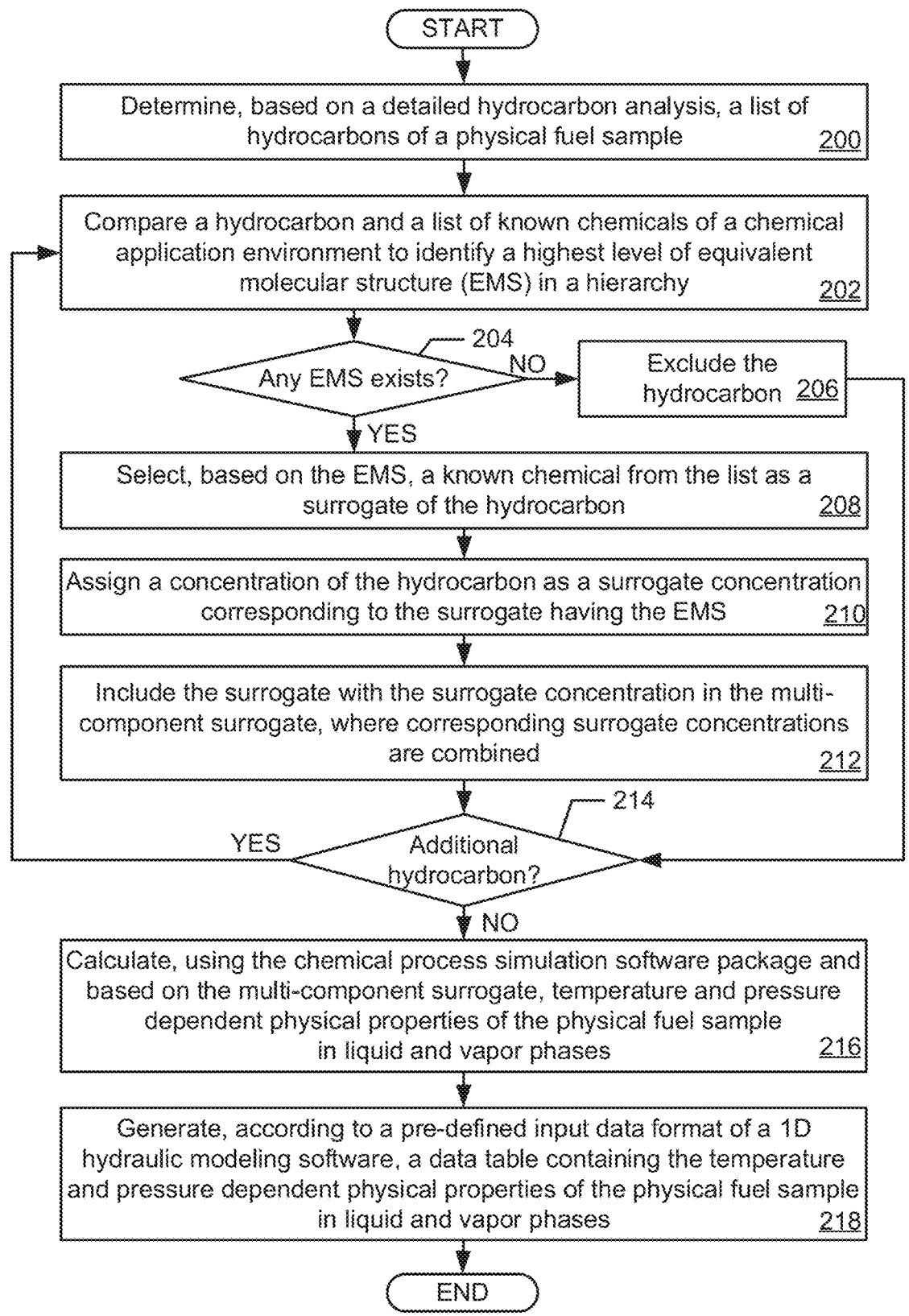
FIG. 2 shows a flowchart in accordance with one or more embodiments.

Turning to FIG. 2, FIG. 2 shows a flowchart in accordance with one or more embodiments. Specifically, FIG. 2 describes a method of generating a multi-component surrogate to represent a real fuel sample during 1D hydraulic modeling to design or improve a DI system. One or more blocks in FIG. 2 may be performed using one or more components as described in FIG. 1. While the various blocks in FIG. 2 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

Initially in Block 200, a list of hydrocarbons of a physical fuel sample is determined by performing a detailed hydrocarbon analysis. In one or more embodiments, the physical fuel sample is obtained from a laboratory, a petroleum refinery, or a gas station. The detailed hydrocarbon analysis may be performed using any existing standardized test method (e.g., according to American Society for Testing and Materials (ASTM) D6730).

In Block 202, a hydrocarbon in the physical fuel sample is compared to a list of known chemicals of a chemical process software package to identify a highest level of equivalent molecular structure. The highest level of equivalent molecular structure is identified based on a hierarchy of equivalent molecular structures. An example hierarchy is shown in TABLE 1 below.

As shown in TABLE 1, the hierarchy starts from the highest level of an identical molecular structure and goes down to the lowest level according to the sequence of the initial level, the first level, the second level, the third level, the fourth level, the fifth level, and the sixth level.

Table 1
- an identical molecular structure
- a first level equivalent molecular structure of stereoisomer
- a second level equivalent molecular structure of structural isomer
- a third level equivalent molecular structure containing the same number of carbon atoms in branches from the main carbon chain, belonging to the same hydrocarbon type class, and having the same number of total carbon atoms
- a fourth level equivalent molecular structure of same hydrocarbon type and total number of carbon atoms
- a fifth level equivalent molecular structure of same number of rings and total carbon number
- a sixth level equivalent molecular structure of same total number of carbon atoms.

For example, if a hydrocarbon identified in the sample has the first level equivalent molecular structure of stereoisomer compared to one or more known chemicals and also has the fourth level equivalent molecular structure of same hydrocarbon type and total carbon number compared to a larger set of known chemicals, the first level equivalent molecular structure of stereoisomer is selected as the equivalent molecular structure. In other words, the one or more known chemicals are stereoisomers of the hydrocarbon, while the larger set of known chemicals are similar to the hydrocarbon as having same hydrocarbon type and total carbon number. In one or more embodiments, the hierarchy of equivalent molecular structures may have more or fewer levels than the example shown in TABLE 1.

In Block 204, a determination is made as to whether any equivalent molecular structure (EMS) is identified. If the determination is negative, i.e., no EMS of the hydrocarbon exists in the list of known chemicals of the chemical process software package, the method proceeds to Block 206. In Block 206, the hydrocarbon without any EMS in the list of known chemicals is identified as an unknown hydrocarbon and excluded from the multi-component surrogate. The method then proceeds to Block 214. If the determination in Block 204 is positive, i.e., at least one EMS of the hydrocarbon exists in the list of known chemicals, the method proceeds to Block 208.

In Block 208, one or more known chemicals having the equivalent molecular structure, as compared to the hydrocarbon, are selected from the list of known chemicals as surrogates of the hydrocarbon.

In Block 210, a concentration of the hydrocarbon in the physical fuel sample is divided into a number of surrogate concentrations each corresponding to one of the surrogates of the hydrocarbon. For example, if stereoisomers of the hydrocarbon are selected from the list of known chemicals as surrogates of the hydrocarbon, the real concentration of the hydrocarbon is divided into equal shares of surrogate concentrations where each surrogate concentration is assigned to one of the stereoisomers.

In Block 212, the multi-component surrogate is iteratively generated by including the surrogates selected in Block 208 with the corresponding surrogate concentrations generated in Block 210. By iterating from Block 202 through Block 212, the multi-component surrogate includes surrogates of all hydrocarbons in the real fuel sample with the exception of unknown hydrocarbons, if any, excluded in Block 206. Generally, the equivalent molecular structures of different hydrocarbons may be at different levels in the hierarchy of equivalent molecular structures. The combined surrogate concentrations of all hydrocarbons in the multi-component surrogate are normalized subsequent to excluding all unknown hydrocarbons. In other words, the surrogate concentrations of all surrogates in the multi-component surrogate sum up to 100% after normalization.

In Block 216, temperature and pressure dependent physical properties of the physical fuel sample, in liquid and vapor phases, are calculated using the chemical process simulation software package. During the calculation, the hydrocarbons of the fuel sample are represented by the multi-component surrogate consisting of known chemicals of the chemical process simulation software package.

In Block 218, a data table containing the temperature and pressure dependent physical properties of the physical fuel sample, in liquid and vapor phases, is generated. In particular, the data table is generated according to a pre-defined input data format of the 1D hydraulic modeling software. The data table is directly used by the 1D hydraulic model software or used to extract relevant equation constants for indirect property estimation (i.e., enthalpy via specific heat).

Figure 3A:
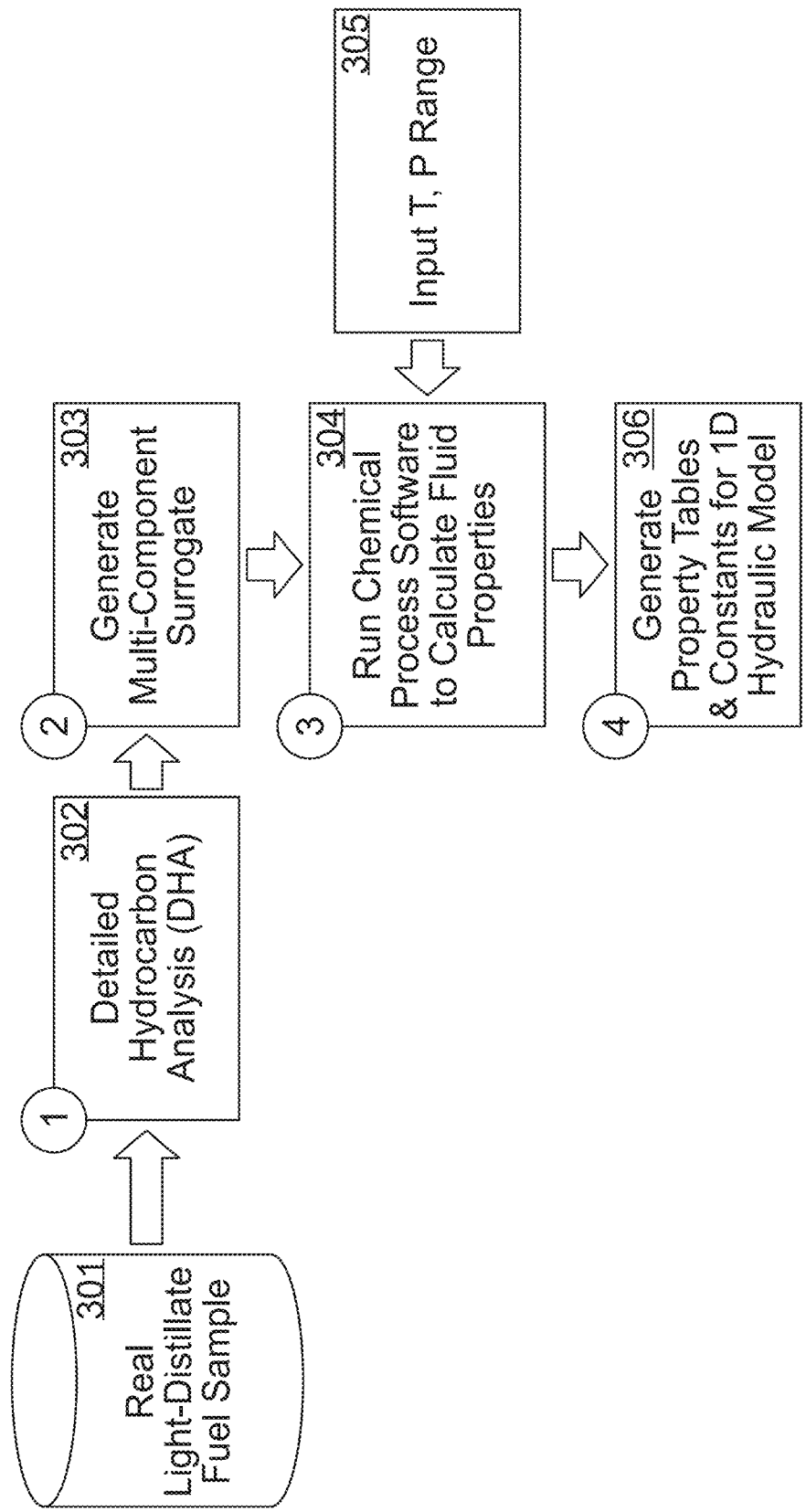
FIGS. 3A, 3B, 3C, and 3D show an example in accordance with one or more embodiments.
Figure 3B:
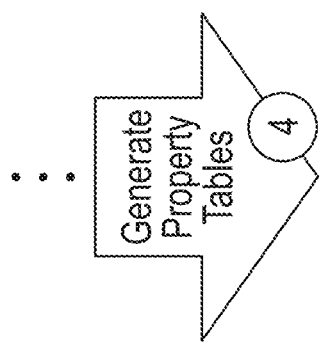
Figure 3B:
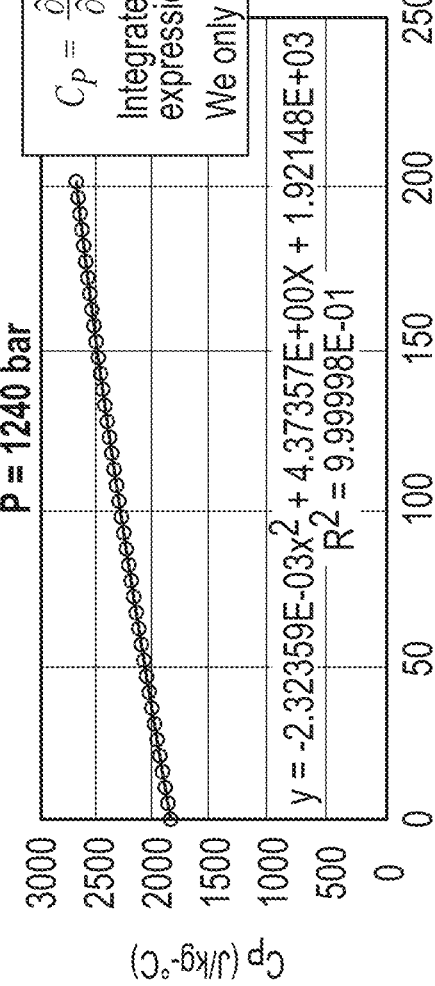

Turning to FIGS. 3A-3B, FIGS. 3A-3B provide an example of modeling the fuel properties of a real fuel sample using a multi-component surrogate in accordance with one or more embodiments. The example shown in FIGS. 3A-3B may be, for example, based on one or more components depicted in FIG. 1 above and the method flowchart depicted in FIG. 2 above. In one or more embodiments, one or more of the modules and/or elements shown in FIGS. 3A-3B may be omitted, repeated, and/or substituted. Accordingly, embodiments of the invention should not be considered limited to the specific arrangements of modules and/or elements shown in FIGS. 3A-3B.

Turning to FIG. 3A, FIG. 3A illustrates an example workflow of modeling the fuel properties of a real fuel sample in a DI system. In Block 301, a real light-distillate fuel sample is obtained, e.g., from a laboratory, a petroleum refinery, or a gas station. In Block 302, all of the individual chemical components (e.g., hydrocarbons) and corresponding concentrations are identified in the real fuel sample. The identification may be performed using an existing standardized test method (e.g., according to American Society for Testing and Materials (ASTM) D6730) referred to as the detailed hydrocarbon analysis (DHA).

In Block 303, the results from the DHA are used to generate a detailed multi-component surrogate that closely resembles the chemical constituents of the real light-distillate fuel sample. In one or more embodiments of the invention, generating the multi-component surrogate is based at least on the molecular structure, carbon number hydrocarbon type, and other characteristics of hydrocarbons that are not available in the pre-configured list of known chemicals of an existing chemical process simulator software. For hydrocarbons identified in the DHA, but which are not in the list of known chemicals, a structurally similar known chemical is identified as a surrogate according to a hierarchy of similar molecular structures. As noted above, in the hierarchy of similar molecular structures, same molecular formula is the top priority, followed by same number of carbons, followed by same hydrocarbon type, etc.

In the multi-component surrogate, surrogate concentrations of the same known chemicals are combined for all hydrocarbons in the real light-distillate fuel sample. Unknown hydrocarbons are eliminated from the multi-component surrogate where the remaining total combined surrogate concentration is renormalized to 100%.

In Block 304, a set of physical properties of the multi-component surrogate in the liquid and vapor phases is generated over the pressure and temperature ranges of interest (represented as Block 305). Specifically, the existing chemical process simulation software (e.g., ASPEN HYSYS) is used to accurately calculate the thermo-physical properties of the multi-component surrogate.

In Block 306, the set of physical properties of the multi-component surrogate is formatted into the tables and equation constants required by the existing 1D hydraulic modeling software package. For example, the output files from the existing chemical process simulation software package (e.g., ASPEN HYSYS) are processed to export relevant data to a format recognized by the 1D hydraulic modeling software package. The properly formatted data may be directly used in 1D hydraulic model software or used to extract relevant equation constants for indirect property estimation (i.e., enthalpy via specific heat).

One of the major distinguishing features of the current invention is that a highly accurate physical surrogate can be generated by accounting for all the identified components in light-distillate fuels via DHA. The process is well suited to activities which only require physical properties, such as 1D hydraulic modeling. However, some 3D computational fluid dynamics (CFD) modeling software packages include an option for the separate designation of physical v.s. chemical kinetic properties, such as CONVERGE. This option allows the additional use of the detailed physical surrogate based on the example workflow depicted in FIG. 3A above to tabulate the relevant properties for subsequent 3D modeling of reacting sprays in combustion environments. For the 3D modeling environment, Block 304 above is extended to include (i) calculating temperature-pressure dependent physical properties of the mixture for both liquid and vapor phases and output as a table, and (ii) calculating temperature-dependent physical properties for the liquid phase and output as a table. Accordingly, Block 306 is extended to include formatting the set of physical properties of the multi-component surrogate into the tables and equation constants required by the existing 1D hydraulic or 3D CFD models.

Turning to FIG. 3B, FIG. 3B illustrates example data from the process flow depicted in FIG. 3A above. In particular, the Block 311 corresponds to Block 302 of FIG. 3A and shows a portion of the detailed hydrocarbon analysis (DHA) results for a particular light-distillate fuel, referred to as "RON60." The portion is not exhaustive as the DHA results contain over a hundred individual hydrocarbons with several more chemical groups that are not shown. The Block 312 corresponds to Block 303 of FIG. 3A and shows known chemicals contributing to the multi-component surrogate that are surrogates of all the entries in the Block 311. These known chemicals are selected during surrogate generation which are chemically representative of the real fuel, but also compatible with the list of known chemicals available in the chemical process software package (e.g., ASPEN HYSYS).

For semi-known hydrocarbons (i.e. those for which the carbon number and carbon type are found in known chemicals, but without the exact structure of the known chemicals) in Block 311, the concentration is redistributed amongst known chemicals with the same carbon number and of the same hydrocarbon or oxygenate type. This ensures that the overall distribution of molecules of the surrogate (by carbon number and by hydrocarbon type) remains consistent with the target fuel.

For semi-known hydrocarbons in Block 311 with no identified members of the same group in the sample, a generic structurally similar chemical is used for which properties exist in the list of known chemicals. The generic structurally similar chemical is selected according to the hierarchy of similar molecular structures. For example, n-tetradecane is used as the surrogate for an unidentified C14 isoparaffin. The list of known chemicals generally contains at least one entry (e.g., a normal paraffin) for every carbon number.

When the chemical process software is run using the multi-component surrogate mixture, it generates the required fluid properties within the temperature and pressure ranges of interest (represented as Block 313). Finally, the fluid properties in Block 313, corresponding to Block 304 of FIG. 3A, are organized into the tables and equation constants required by the 1D hydraulic model software (represented as Block 314 that corresponds to Block 306 of FIG. 3A).

Figure 3C:
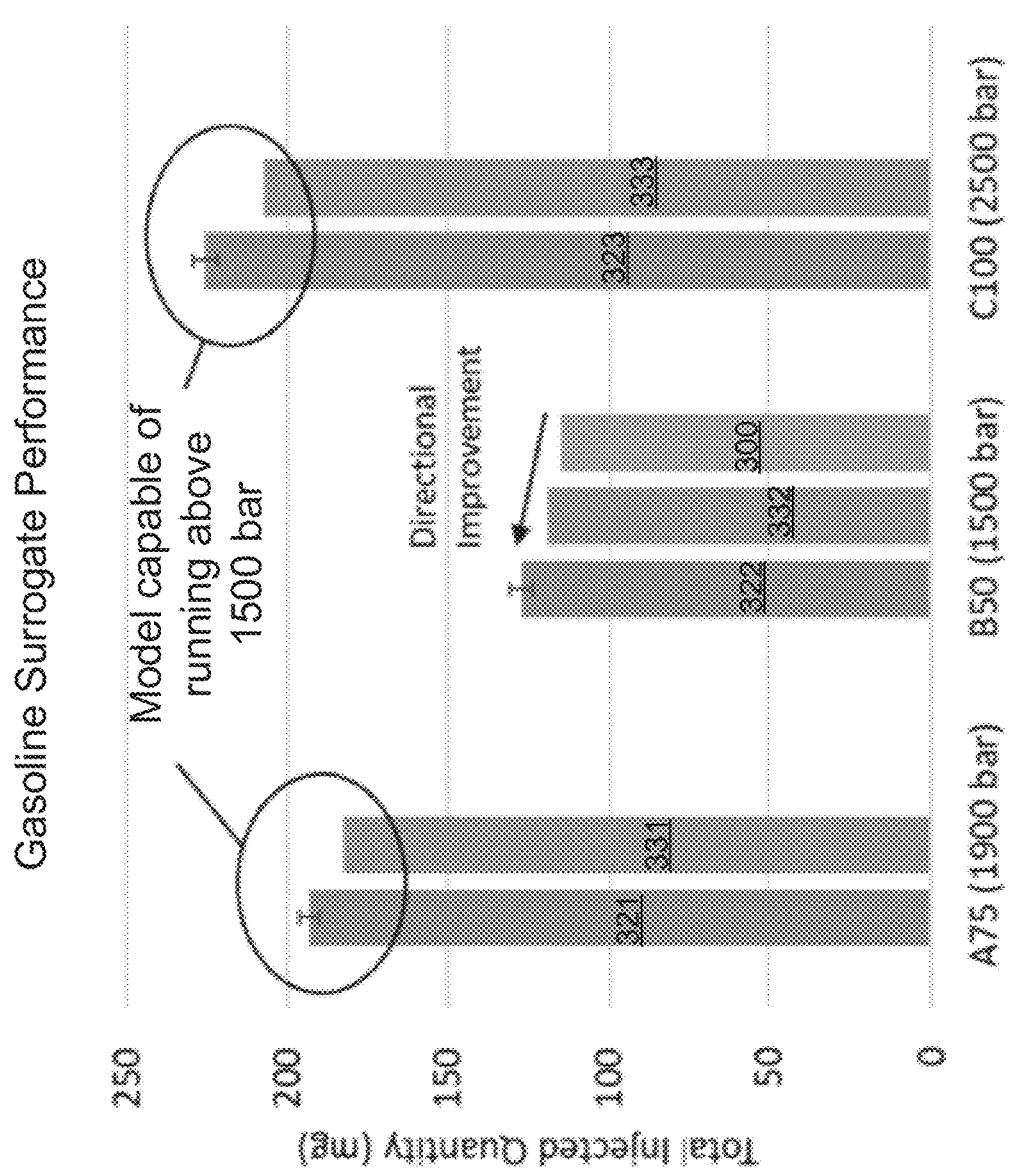

Turning to FIG. 3C, FIG. 3C illustrates example 1D hydraulic modeling results (i.e., A75 at pressure of 1900 bar, B50 at pressure of 1500 bar, and C100 at pressure of 2500 bar) for a particular injector before and after incorporating custom fuel property specifications. In particular, the custom fuel property specifications are generated by the Block 313, and the example 1D hydraulic modeling results (A75, B50, C100) are generated by augmenting the 1D hydraulic modeling engine (Block 103, FIG. 1) with the data from Block 314 in FIG. 3B above.

A shown in FIG. 3C, the bars (321, 322, 323) indicate experimental measurements (i.e., total injected quantity (mg)) quantifying the amount of real RON60 fuel dispensed by the actual physical injector.

The bars (331, 332, 333) indicate 1D hydraulic modeling results generated using the multi-component surrogate shown in Block 312 of FIG. 3B. In other words, the real RON60 fuel is represented by the multi-component surrogate in generating the 1D hydraulic modeling results. Specifically, the 1D hydraulic modeling results (331, 332, 333) are generated using, as input data, the fuel property tables shown in Block 314 of FIG. 3B. Good agreement (with less than 8% difference) between the modeling results (331, 332, 333) and the corresponding experimental measurements (321, 322, 323) is achieved over all pressure conditions 1900 bar, 1500 bar, and 2500 bar. With additional calibration of the hardware components in the 1-D hydraulic model (i.e., adapting orifice discharge coefficients to light-distillates instead of diesel), the 1D hydraulic modeling results (not shown) are further improved to match the corresponding experimental measurements (321, 322, 323) within 4% difference.

In comparison, the bar (300) indicates default 1D hydraulic modeling result without using the multi-component surrogate shown in Block 312 of FIG. 3B. Instead, the default 1D hydraulic modeling result (300) is generated using the only surrogate available (N-heptane) within the 1D hydraulic modeling software package for gasoline or other light-distillate fuels. It can be seen that a relatively large discrepancy exists between the experimental measurements (322) and the default modeling result (300) when using this default single-component surrogate (N-heptane). Furthermore, fuel properties for the N-heptane surrogate do not exist at pressure conditions above 500 bars and cannot be accurately extrapolated to the higher injection pressure conditions of 1900 bar and 2500 bar in the 1D hydraulic modeling software package. Therefore, no default modeling results can be generated for A75 (1900 bar) or C100 (2500 bar) using the default single-component surrogate (N-heptane).

Figure 3D:
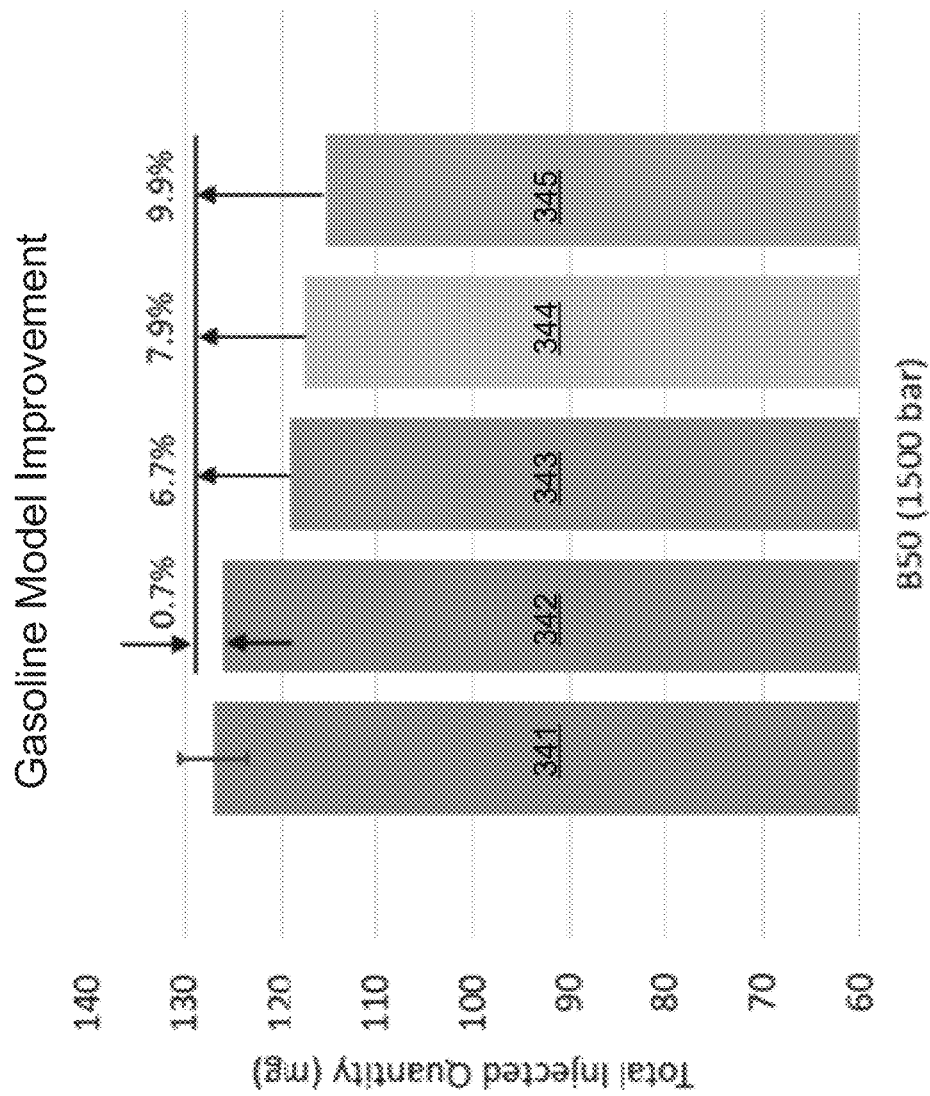

Turning to FIG. 3D, FIG. 3D illustrates example details of the 1D hydraulic modeling results B50 at pressure of 1500 bar shown in FIG. 3C above. A shown in FIG. 3D, the percentages (i.e., 0.7%, 6.7%, 7.9%, and 9.9%) indicate progressive improvements in discrepancy between modeled results, represented as bars (342, 343, 344, 345), and experimental results, represented as bar (341), due to the use of successively more accurate fuel properties and model calibration. The bar (345) represents the initial discrepancy with experimental results represented as bar (341) when using the default single-component surrogate for light distillate fuels (N-heptane) in the 1D hydraulic modeling software. The bar (344) uses the properties tabulated for N-heptane in the chemical process software. There is an improvement relative to the bar (345) because the original N-heptane property database in the 1D model only exists up to pressures of 500 bar and had to be extrapolated to run at the 1500 bar case. The chemical process software model version of N-heptane is properly calculated and tabulated up to the injection pressure of interest. The bar (343) represents the additional improvement gained when implementing the multi-component surrogate for RON60 as determined by the current methodology. The bar (342) shows final model refinement via recalibration of the hydraulic model ultimately exceeding the desired result of less than 5% discrepancy.

Figure 4A:
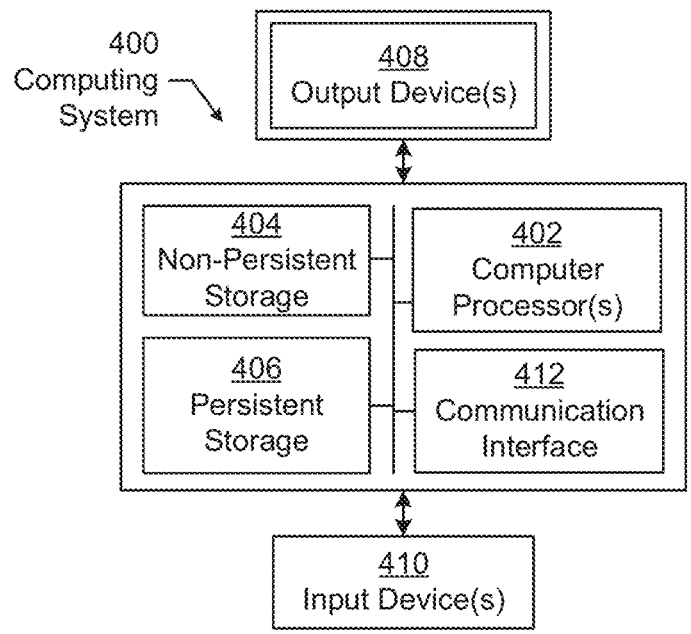
FIGS. 4A and 4B show a computing system in accordance with one or more embodiments.

Embodiments may be implemented on a computing system. Any combination of mobile, desktop, server, router, switch, embedded device, or other types of hardware may be used. For example, as shown in FIG. 4A, the computing system (400) may include one or more computer processors (402), non-persistent storage (404) (e.g., volatile memory, such as random access memory (RAM), cache memory), persistent storage (406) (e.g., a hard disk, an optical drive such as a compact disk (CD) drive or digital versatile disk (DVD) drive, a flash memory, etc.), a communication interface (412) (e.g., Bluetooth interface, infrared interface, network interface, optical interface, etc.), and numerous other elements and functionalities.

The computer processor(s) (402) may be an integrated circuit for processing instructions. For example, the computer processor(s) may be one or more cores or micro-cores of a processor. The computing system (400) may also include one or more input devices (410), such as a touchscreen, keyboard, mouse, microphone, touchpad, electronic pen, or any other type of input device.

The communication interface (412) may include an integrated circuit for connecting the computing system (400) to a network (not shown) (e.g., a local area network (LAN), a wide area network (WAN) such as the Internet, mobile network, or any other type of network) and/or to another device, such as another computing device.

Further, the computing system (400) may include one or more output devices (405), such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) (402), non-persistent storage (404), and persistent storage (406). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the disclosure.

Figure 4B:
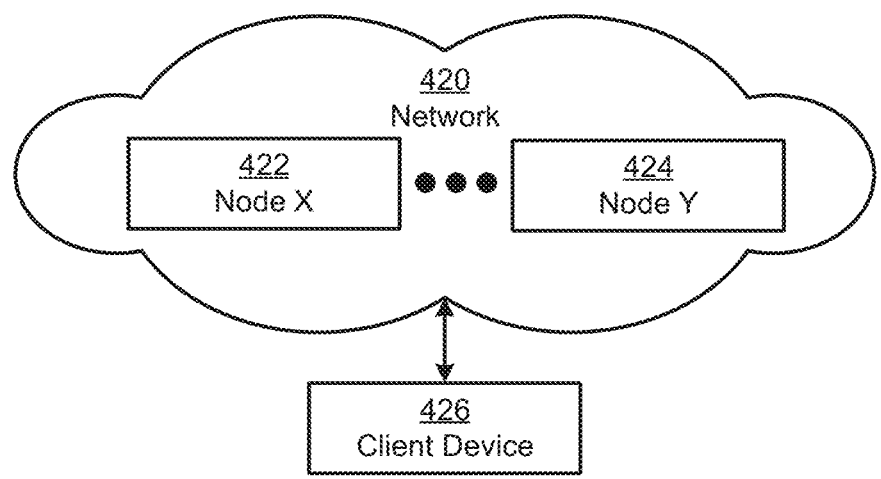

The computing system (400) in FIG. 4A may be connected to or be a part of a network. For example, as shown in FIG. 4B, the network (420) may include multiple nodes (e.g., node X (422), node Y (424)). Each node may correspond to a computing system, such as the computing system shown in FIG. 4A, or a group of nodes combined may correspond to the computing system shown in FIG. 4A. By way of an example, embodiments of the disclosure may be implemented on a node of a distributed system that is connected to other nodes. By way of another example, embodiments of the disclosure may be implemented on a distributed computing system having multiple nodes, where each portion of the disclosure may be located on a different node within the distributed computing system. Further, one or more elements of the aforementioned computing system (400) may be located at a remote location and connected to the other elements over a network.

Although not shown in FIG. 4B, the node may correspond to a blade in a server chassis that is connected to other nodes via a backplane. By way of another example, the node may correspond to a server in a data center. By way of another example, the node may correspond to a computer processor or micro-core of a computer processor with shared memory and/or resources.

The nodes (e.g., node X (422), node Y (424)) in the network (420) may be configured to provide services for a client device (426). For example, the nodes may be part of a cloud computing system. The nodes may include functionality to receive requests from the client device (426) and transmit responses to the client device (426). The client device (426) may be a computing system, such as the computing system shown in FIG. 4A. Further, the client device (426) may include and/or perform all or a portion of one or more embodiments of the disclosure.

The computing system or group of computing systems described in FIGS. 4A and 4B may include functionality to perform a variety of operations disclosed herein. For example, the computing system(s) may perform communication between processes on the same or different systems. A variety of mechanisms, employing some form of active or passive communication, may facilitate the exchange of data between processes on the same device. Examples representative of these inter-process communications include, but are not limited to, the implementation of a file, a signal, a socket, a message queue, a pipeline, a semaphore, shared memory, message passing, and a memory-mapped file. Further details pertaining to a couple of these non-limiting examples are provided below.

Based on the client-server networking model, sockets may serve as interfaces or communication channel endpoints enabling bidirectional data transfer between processes on the same device. Foremost, following the client-server networking model, a server process (e.g., a process that provides data) may create a first socket object. Next, the server process binds the first socket object, thereby associating the first socket object with a unique name and/or address. After creating and binding the first socket object, the server process then waits and listens for incoming connection requests from one or more client processes (e.g., processes that seek data). At this point, when a client process wishes to obtain data from a server process, the client process starts by creating a second socket object. The client process then proceeds to generate a connection request that includes at least the second socket object and the unique name and/or address associated with the first socket object. The client process then transmits the connection request to the server process. Depending on availability, the server process may accept the connection request, establishing a communication channel with the client process, or the server process, busy in handling other operations, may queue the connection request in a buffer until the server process is ready. An established connection informs the client process that communications may commence. In response, the client process may generate a data request specifying the data that the client process wishes to obtain. The data request is subsequently transmitted to the server process. Upon receiving the data request, the server process analyzes the request and gathers the requested data. Finally, the server process then generates a reply including at least the requested data and transmits the reply to the client process. The data may be transferred, more commonly, as datagrams or a stream of characters (e.g., bytes).

Shared memory refers to the allocation of virtual memory space in order to substantiate a mechanism for which data may be communicated and/or accessed by multiple processes. In implementing shared memory, an initializing process first creates a shareable segment in persistent or non-persistent storage. Post creation, the initializing process then mounts the shareable segment, subsequently mapping the shareable segment into the address space associated with the initializing process. Following the mounting, the initializing process proceeds to identify and grant access permission to one or more authorized processes that may also write and read data to and from the shareable segment. Changes made to the data in the shareable segment by one process may immediately affect other processes, which are also linked to the shareable segment. Further, when one of the authorized processes accesses the shareable segment, the shareable segment maps to the address space of that authorized process. Often, one authorized process may mount the shareable segment, other than the initializing process, at any given time.

Other techniques may be used to share data, such as the various data described in the present application, between processes without departing from the scope of the disclosure. The processes may be part of the same or different application and may execute on the same or different computing system.

Rather than or in addition to sharing data between processes, the computing system performing one or more embodiments of the disclosure may include functionality to receive data from a user. For example, in one or more embodiments, a user may submit data via a graphical user interface (GUI) on the user device. Data may be submitted via the graphical user interface by a user selecting one or more graphical user interface widgets or inserting text and other data into graphical user interface widgets using a touchpad, a keyboard, a mouse, or any other input device. In response to selecting a particular item, information regarding the particular item may be obtained from persistent or non-persistent storage by the computer processor. Upon selection of the item by the user, the contents of the obtained data regarding the particular item may be displayed on the user device in response to the user's selection.

By way of another example, a request to obtain data regarding the particular item may be sent to a server operatively connected to the user device through a network. For example, the user may select a uniform resource locator (URL) link within a web client of the user device, thereby initiating a Hypertext Transfer Protocol (HTTP) or other protocol request being sent to the network host associated with the URL. In response to the request, the server may extract the data regarding the particular selected item and send the data to the device that initiated the request. Once the user device has received the data regarding the particular item, the contents of the received data regarding the particular item may be displayed on the user device in response to the user's selection. Further to the above example, the data received from the server after selecting the URL link may provide a web page in Hyper Text Markup Language (HTML) that may be rendered by the web client and displayed on the user device.

Once data is obtained, such as by using techniques described above or from storage, the computing system, in performing one or more embodiments of the disclosure, may extract one or more data items from the obtained data. For example, the extraction may be performed as follows by the computing system (400) in FIG. 4A. First, the organizing pattern (e.g., grammar, schema, layout) of the data is determined, which may be based on one or more of the following: position (e.g., bit or column position, Nth token in a data stream, etc.), attribute (where the attribute is associated with one or more values), or a hierarchical/tree structure (consisting of layers of nodes at different levels of detail—such as in nested packet headers or nested document sections). Then, the raw, unprocessed stream of data symbols is parsed, in the context of the organizing pattern, into a stream (or layered structure) of tokens (where each token may have an associated token "type").

Next, extraction criteria are used to extract one or more data items from the token stream or structure, where the extraction criteria are processed according to the organizing pattern to extract one or more tokens (or nodes from a layered structure). For position-based data, the token(s) at the position(s) identified by the extraction criteria are extracted. For attribute/value-based data, the token(s) and/or node(s) associated with the attribute(s) satisfying the extraction criteria are extracted. For hierarchical/layered data, the token(s) associated with the node(s) matching the extraction criteria are extracted. The extraction criteria may be as simple as an identifier string or may be a query presented to a structured data repository (where the data repository may be organized according to a database schema or data format, such as XML).

The extracted data may be used for further processing by the computing system. For example, the computing system of FIG. 4A, while performing one or more embodiments of the disclosure, may perform data comparison. Data comparison may be used to compare two or more data values (e.g., A, B). For example, one or more embodiments may determine whether $A>B$, $A=B$, $A!=B$, $A<B$, etc. The comparison may be performed by submitting A, B, and an opcode specifying an operation related to the comparison into an arithmetic logic unit (ALU) (i.e., circuitry that performs arithmetic and/or bitwise logical operations on the two data values). The ALU outputs the numerical result of the operation and/or one or more status flags related to the numerical result. For example, the status flags may indicate whether the numerical result is a positive number, a negative number, zero, etc. By selecting the proper opcode and then reading the numerical results and/or status flags, the comparison may be executed. For example, in order to determine if $A>B$, B may be subtracted from A (i.e., A-B), and the status flags may be read to determine if the result is positive (i.e., if $A>B$, then $A-B>0$). In one or more embodiments, B may be considered a threshold, and A is deemed to satisfy the threshold if $A=B$ or if $A>B$, as determined using the ALU. In one or more embodiments of the disclosure, A and B may be vectors, and comparing A with B includes comparing the first element of vector A with the first element of vector B, the second element of vector A with the second element of vector B, etc. In one or more embodiments, if A and B are strings, the binary values of the strings may be compared.

The computing system in FIG. 4A may implement and/or be connected to a data repository. For example, one type of data repository is a database. A database is a collection of information configured for ease of data retrieval, modification, re-organization, and deletion. Database Management System (DBMS) is a software application that provides an interface for users to define, create, query, update, or administer databases.

The user, or software application, may submit a statement or query into the DBMS. Then the DBMS interprets the statement. The statement may be a select statement to request information, update statement, create statement, delete statement, etc. Moreover, the statement may include parameters that specify data, or data container (database, table, record, column, view, etc.), identifier(s), conditions (comparison operators), functions (e.g. join, full join, count, average, etc.), sort (e.g. ascending, descending), or others. The DBMS may execute the statement. For example, the DBMS may access a memory buffer, a reference or index a file for read, write, deletion, or any combination thereof, for responding to the statement. The DBMS may load the data from persistent or non-persistent storage and perform computations to respond to the query. The DBMS may return the result(s) to the user or software application.

The computing system of FIG. 4A may include functionality to present raw and/or processed data, such as results of comparisons and other processing. For example, presenting data may be accomplished through various presenting methods. Specifically, data may be presented through a user interface provided by a computing device. The user interface may include a GUI that displays information on a display device, such as a computer monitor or a touchscreen on a handheld computer device. The GUI may include various GUI widgets that organize what data is shown as well as how data is presented to a user. Furthermore, the GUI may present data directly to the user, e.g., data presented as actual data values through text, or rendered by the computing device into a visual representation of the data, such as through visualizing a data model.

For example, a GUI may first obtain a notification from a software application requesting that a particular data object be presented within the GUI. Next, the GUI may determine a data object type associated with the particular data object, e.g., by obtaining data from a data attribute within the data object that identifies the data object type. Then, the GUI may determine any rules designated for displaying that data object type, e.g., rules specified by a software framework for a data object class or according to any local parameters defined by the GUI for presenting that data object type. Finally, the GUI may obtain data values from the particular data object and render a visual representation of the data values within a display device according to the designated rules for that data object type.

Data may also be presented through various audio methods. In particular, data may be rendered into an audio format and presented as sound through one or more speakers operably connected to a computing device.

Data may also be presented to a user through haptic methods. For example, haptic methods may include vibrations or other physical signals generated by the computing system. For example, data may be presented to a user using a vibration generated by a handheld computer device with a predefined duration and intensity of the vibration to communicate the data.

The above description of functions presents only a few examples of functions performed by the computing system of FIG. 4A and the nodes and/or client device in FIG. 4B. Other functions may be performed using one or more embodiments of the disclosure.

While the disclosure has been described with respect to a limited number of embodiments, those skilled in the art, having benefit of this disclosure, will appreciate that other embodiments can be devised which do not depart from the scope of the disclosure as disclosed herein. Accordingly, the scope of the disclosure should be limited only by the attached claims.

Although the preceding description has been described herein with reference to particular means, materials and embodiments, it is not intended to be limited to the particulars disclosed herein; rather, it extends to all functionally equivalent structures, methods and uses, such as are within the scope of the appended claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed is:

1. A method to improve performance of an internal combustion engine, the method comprising:
   determining, based on a detailed hydrocarbon analysis, a plurality of components of a physical fuel sample;
   selecting, by a computer processor and for a first hydrocarbon of the plurality of hydrocarbons, a first plurality of chemicals from a list of known chemicals in a chemical property database, chemical property correlation software, or chemical process software package, the first hydrocarbon having a first equivalent molecular structure as each of the first plurality of chemicals;
   dividing, by the computer processor, a first concentration of the first hydrocarbon in the physical fuel sample into a first plurality of surrogate concentrations corresponding to the first plurality of chemicals;
   generating, by the computer processor, a multi-component surrogate based at least on the first plurality of surrogate concentrations, wherein each of the first plurality of chemicals represents the first hydrocarbon as a surrogate in the multi-component surrogate;
   generating, by using the multi-component surrogate to represent the physical fuel sample in a one-dimensional (1D) hydraulic modeling software, modelling results of a direct injection (DI) system of the internal combustion engine, the modeling results comprising calculated interaction between the physical fuel sample and mechanical components in the DI system; and
   refining, based on the modelling results, structural features of the mechanical components in the DI system to improve the performance of the internal combustion engine,
   wherein the refining comprises:
      assessing efficacy of hardware design changes of the mechanical components in said improving the performance of the internal combustion engine; and
      performing an experiment where an amount of the physical fuel sample is dispensed using an actual physical injector to obtain an experimental performance measurement,
   wherein the experimental performance measurement substantially matches a modeled performance measurement in the modeling results.

2. The method according to claim 1, further comprising selecting the first equivalent molecular structure from a hierarchy of equivalent molecular structures, the hierarchy comprising:
   an identical molecular structure,
   a first level equivalent molecular structure of stereoisomer,
   a second level equivalent molecular structure of structural isomer, a third level equivalent molecular structure of same carbon number and carbon type in each and every molecular branch,
a fourth level equivalent molecular structure of same carbon types and total carbon number,
a fifth level equivalent molecular structure of same number of rings and total carbon number, and
a sixth level equivalent molecular structure of same total carbon number.

3. The method according to claim 2, further comprising:
comparing the first hydrocarbon and the list of known chemicals of the chemical process software package to identify one or more levels of equivalent molecular structures in the hierarchy,
wherein the first equivalent molecular structure is selected from the hierarchy based on a highest level in the one or more levels of the equivalent molecular structures.

4. The method according to claim 3, further comprising:
selecting, for a second hydrocarbon of the plurality of hydrocarbons, a second plurality of chemicals from the list of known chemicals of the chemical process software package, the second hydrocarbon having a second equivalent molecular structure as each of the second plurality of chemicals; and
dividing a second concentration of the second hydrocarbon in the physical fuel sample into a second plurality of surrogate concentrations corresponding to the second plurality of chemicals,
wherein generating the multi-component surrogate comprises combining the first plurality of surrogate concentrations and the second plurality of surrogate concentrations for each chemical in a combination of the first plurality of chemicals and the second plurality of chemicals.

5. The method according to claim 4, wherein the first equivalent molecular structure and the second equivalent molecular structure correspond to different levels in the hierarchy of equivalent molecular structures.

6. The method according to claim 4, further comprising:
selecting, from the plurality of hydrocarbons, all unknown hydrocarbons each having a different carbon number than all chemicals in the list of known chemicals of the chemical process software package,
wherein all the unknown hydrocarbons are excluded from the multi-component surrogate, and
wherein the first plurality of surrogate concentrations and the second plurality of surrogate concentrations, as combined, are normalized in the multi-component surrogate subsequent to excluding all the unknown hydrocarbons.

7. The method according to claim 1, further comprising:
calculating, using the chemical process simulation software package, temperature and pressure dependent physical properties of the physical fuel sample in liquid and vapor phases, wherein the plurality of hydrocarbons of the fuel sample are mapped into the list of known chemicals as the multi-component surrogate; and
generating, according to a pre-defined input data format of the 1D hydraulic modeling software, a data table based on the temperature and pressure dependent physical properties of the physical fuel sample in liquid and vapor phases.

8. A computer system to improve performance of an internal combustion engine, comprising:
a processor; and
a memory coupled to the processor and storing instructions, the instructions, when executed by the processor, comprising functionality for:
determining, based on a detailed hydrocarbon analysis, a plurality of hydrocarbons of a physical fuel sample;
selecting, for a first hydrocarbon of the plurality of hydrocarbons, a first plurality of chemicals from a list of known chemicals of a chemical process software package, the first hydrocarbon having a first equivalent molecular structure as each of the first plurality of chemicals;
dividing a first concentration of the first hydrocarbon in the physical fuel sample into a first plurality of surrogate concentrations corresponding to the first plurality of chemicals;
generating a multi-component surrogate based at least on the first plurality of surrogate concentrations, wherein each of the first plurality of chemicals represents the first hydrocarbon as a surrogate in the multi-component surrogate;
generating, by using the multi-component surrogate to represent the physical fuel sample in a one-dimensional (1D) hydraulic modeling software, modelling results of a direct injection (DI) system of the internal combustion engine, the modeling results comprising calculated interaction between the physical fuel sample and mechanical components in the DI system; and
refining, based on the modelling results, structural features of the mechanical components in the DI system to improve the performance of the internal combustion engine,
wherein the refining comprises:
assessing efficacy of hardware design changes of the mechanical components in said improving the performance of the internal combustion engine; and
performing an experiment where an amount of the physical fuel sample is dispensed using an actual physical injector to obtain an experimental performance measurement,
wherein the experimental performance measurement substantially matches a modeled performance measurement in the modeling results.

9. The computer system according to claim 8, the instructions, when executed by the processor, further comprising functionality for:
selecting the first equivalent molecular structure from a hierarchy of equivalent molecular structures,
wherein the hierarchy comprises:
an identical molecular structure,
a first level equivalent molecular structure of stereoisomer,
a second level equivalent molecular structure of structural isomer,
a third level equivalent molecular structure of same carbon number and carbon type in each and every molecular branch,
a fourth level equivalent molecular structure of same carbon types and total carbon number,
a fifth level equivalent molecular structure of same number of rings and total carbon number, and
a sixth level equivalent molecular structure of same total carbon number.

10. The computer system according to claim 9, the instructions, when executed by the processor, further comprising functionality for:

comparing the first hydrocarbon and the list of known chemicals of the chemical process software package to identify one or more levels of equivalent molecular structures in the hierarchy, wherein the first equivalent molecular structure is selected from the hierarchy based on a highest level in the one or more levels of the equivalent molecular structures.

11. The computer system according to claim 10, the instructions, when executed by the processor, further comprising functionality for:

selecting, for a second hydrocarbon of the plurality of hydrocarbons, a second plurality of chemicals from the list of known chemicals of the chemical process software package, the second hydrocarbon having a second equivalent molecular structure as each of the second plurality of chemicals; and dividing a second concentration of the second hydrocarbon in the physical fuel sample into a second plurality of surrogate concentrations corresponding to the second plurality of chemicals, wherein generating the multi-component surrogate comprises combining the first plurality of surrogate concentrations and the second plurality of surrogate concentrations for each chemical in a combination of the first plurality of chemicals and the second plurality of chemicals.

12. The computer system according to claim 11, wherein the first equivalent molecular structure and the second equivalent molecular structure correspond to different levels in the hierarchy of equivalent molecular structures.

13. The computer system according to claim 11, the instructions, when executed by the processor, further comprising functionality for:

selecting, from the plurality of hydrocarbons, all unknown hydrocarbons each having a different carbon number than all chemicals in the list of known chemicals of the chemical process software package, wherein all the unknown hydrocarbons are excluded from the multi-component surrogate, and wherein the first plurality of surrogate concentrations and the second plurality of surrogate concentrations, as combined, are normalized in the multi-component surrogate subsequent to excluding all the unknown hydrocarbons.

14. The computer system according to claim 8, the instructions, when executed by the processor, further comprising functionality for:

calculating, using the chemical process simulation software package, temperature and pressure dependent physical properties of the physical fuel sample in liquid and vapor phases, wherein the plurality of hydrocarbons of the fuel sample are mapped into the list of known chemicals as the multi-component surrogate; and generating, according to a pre-defined input data format of the 1D hydraulic modeling software, a data table based on the temperature and pressure dependent physical properties of the physical fuel sample in liquid and vapor phases.

15. A non-transitory computer readable medium storing instructions executable by a computer processor to improve performance of an internal combustion engine, the instructions comprising functionality for:

determining, based on a detailed hydrocarbon analysis, a plurality of hydrocarbons of a physical fuel sample;

selecting, for a first hydrocarbon of the plurality of hydrocarbons, a first plurality of chemicals from a list of known chemicals of a chemical process software package, the first hydrocarbon having a first equivalent molecular structure as each of the first plurality of chemicals;

dividing a first concentration of the first hydrocarbon in the physical fuel sample into a first plurality of surrogate concentrations corresponding to the first plurality of chemicals;

generating a multi-component surrogate based at least on the first plurality of surrogate concentrations, wherein each of the first plurality of chemicals represents the first hydrocarbon as a surrogate in the multi-component surrogate;

generating, by using the multi-component surrogate to represent the physical fuel sample in a one-dimensional (1D) hydraulic modeling software, modelling results of a direct injection (DI) system of the internal combustion engine, the modeling results comprising calculated interaction between the physical fuel sample and mechanical components in the DI system; and refining, based on the modelling results, structural features of the mechanical components in the DI system to improve the performance of the internal combustion engine, wherein the refining comprises:

assessing efficacy of hardware design changes of the mechanical components in said improving the performance of the internal combustion engine; and performing an experiment where an amount of the physical fuel sample is dispensed using an actual physical injector to obtain an experimental performance measurement, wherein the experimental performance measurement substantially matches a modeled performance measurement in the modeling results.

16. The non-transitory computer readable medium according to claim 15, the instructions further comprising functionality for:

selecting the first equivalent molecular structure from a hierarchy of equivalent molecular structures, wherein the hierarchy comprises:

an identical molecular structure, a first level equivalent molecular structure of stereoisomer, a second level equivalent molecular structure of structural isomer, a third level equivalent molecular structure of same carbon number and carbon type in each and every molecular branch, a fourth level equivalent molecular structure of same carbon types and total carbon number, a fifth level equivalent molecular structure of same number of rings and total carbon number, and a sixth level equivalent molecular structure of same total carbon number.

17. The non-transitory computer readable medium according to claim 16, the instructions further comprising functionality for:

comparing the first hydrocarbon and the list of known chemicals of the chemical process software package to identify one or more levels of equivalent molecular structures in the hierarchy, wherein the first equivalent molecular structure is selected from the hierarchy based on a highest level in the one or more levels of the equivalent molecular structures.

18. The non-transitory computer readable medium according to claim 17, the instructions further comprising functionality for:
- selecting, for a second hydrocarbon of the plurality of hydrocarbons, a second plurality of chemicals from the list of known chemicals of the chemical process software package, the second hydrocarbon having a second equivalent molecular structure as each of the second plurality of chemicals; and
- dividing a second concentration of the second hydrocarbon in the physical fuel sample into a second plurality of surrogate concentrations corresponding to the second plurality of chemicals,
- wherein generating the multi-component surrogate comprises combining the first plurality of surrogate concentrations and the second plurality of surrogate concentrations for each chemical in a combination of the first plurality of chemicals and the second plurality of chemicals.

19. The non-transitory computer readable medium according to claim 18, wherein the first equivalent molecular structure and the second equivalent molecular structure correspond to different levels in the hierarchy of equivalent molecular structures.

20. The non-transitory computer readable medium according to claim 18, the instructions further comprising functionality for:
- selecting, from the plurality of hydrocarbons, all unknown hydrocarbons each having a different carbon number than all chemicals in the list of known chemicals of the chemical process software package,
- wherein all the unknown hydrocarbons are excluded from the multi-component surrogate, and
- wherein the first plurality of surrogate concentrations and the second plurality of surrogate concentrations, as combined, are normalized in the multi-component surrogate subsequent to excluding all the unknown hydrocarbons.

* * * * *